United States Patent [19]

Moore et al.

[11] Patent Number: 5,237,081
[45] Date of Patent: Aug. 17, 1993

[54] PREPARATION OF INDIUM ALKOXIDES SOLUBLE IN ORGANIC SOLVENTS

[75] Inventors: Christopher P. Moore, Harrow, England; Danielle M. Wettling, Chalon sur Saone Cedex, France

[73] Assignee: Eastman Kodak Company, Rochester, N.Y.

[21] Appl. No.: 927,524
[22] PCT Filed: Mar. 8, 1991
[86] PCT No.: PCT/EP91/00436
 § 371 Date: Sep. 15, 1992
 § 102(e) Date: Sep. 15, 1992
[87] PCT Pub. No.: WO91/13848
 PCT Pub. Date: Sep. 19, 1991

[30] Foreign Application Priority Data

Mar. 16, 1990 [FR] France .................. 90 03646

[51] Int. Cl.$^5$ ............................................. C07F 5/00
[52] U.S. Cl. ................................................... 556/1
[58] Field of Search ........................................ 556/1

[56] References Cited

U.S. PATENT DOCUMENTS

| | | | |
|---|---|---|---|
| 3,641,077 | 2/1972 | Rochow | 260/429 R |
| 3,946,056 | 3/1976 | Thomas | 260/429.7 |
| 4,391,742 | 7/1983 | Steigerwald et al. | 252/512 |
| 4,681,959 | 7/1987 | Ayen et al. | 556/54 |

FOREIGN PATENT DOCUMENTS 63-201138 8/1988 Japan.
1310381 5/1987 U.S.S.R.

OTHER PUBLICATIONS

S. R. Bindal and R. C. Mehrotra, "A Study of Indium Alkoxides In(OR)", *J. Indian Chem. Soc.*, vol. LIII, Sep. 1976, pp. 867–869.

*Primary Examiner*—José G. Dees
*Assistant Examiner*—Porfirio Nazario-Gonzalez
*Attorney, Agent, or Firm*—L. George Legg

[57] ABSTRACT

The invention relates to a process for preparing indium alkoxides soluble in organic solvents.

The preparation method consists in reacting an indium halide with a $C_3$–$C_{20}$ alcohol in the presence of a base having a pka >10 and a low nucleophilicity, in anhydrous medium, under inert gas and in the presence of polar organic solvents.

The invention allows to obtain with a high yield pure indium alkoxides.

19 Claims, No Drawings

PREPARATION OF INDIUM ALKOXIDES SOLUBLE IN ORGANIC SOLVENTS

The invention relates to the preparation of indium alkoxides. More particularly, the invention allows to obtain pure indium alkoxides with a high yield, which are soluble in organic solvents and useful for coating applications, for example to form conductive transparent thin films.

Few examples of the synthesis of indium alkoxides are given in the literature. An article of *J. Indian Chem. Soc*, Vol LIII, Sep. 1976, pp. 867–869 entitled "A study of Indium Alkoxides In(OR)$_3$" describes a preparation of indium tri-isopropoxide by refluxing anhydrous indium trichloride with isopropanol in the presence of sodium isopropoxide. By alcoholysis of indium tri-isopropoxide, other alkoxides can be obtained. However, indium isopropoxide and the resulting alkoxides are unlikely to be pure and contain sodium, which is not acceptable for certain applications where a high conductivity is desired; moreover, these products are not very soluble in organic solvents and are very sensitive to air, which makes them unsuitable for coating applications.

Other patents describe the synthesis of metal alkoxides consisting in reacting a metal halide with an alcohol in a basic medium.

For example U.S. Pat. No. 3,946,056 discloses a two step method to prepare stannic alkoxides. First stannic chloride is reacted with an alkylamine, preferably a dimethylamine or a trimethylamine, then the product obtained is reacted with a tertiary alcohol. The said method is not applicable to indium since the compound formed in the first step, a indium chloride/alkylamine complex is highly stable and does not further react with the alcohol.

U.S. Pat. No. 4,681,959 discloses the preparation of metal alkoxides insoluble in organic solvents, such as methoxides. In an embodiment, the preparation is a one-step process, wherein the metal halide is reacted with the alcohol in the presence of a hydrogen halide acceptor which can be an alkylamine, e.g. trimethylamine. The said hydrogen halide acceptor forms with the amine a compound soluble in reaction solvents while the alkoxide remains soluble in said solvents. Although all the examples relate to titanium alkoxides, the invention can be applied to the preparation of indium alkoxides insoluble in organic solvents. Such alkoxides are unsuitable for the preparation of coating compositions comprising organic solvents.

In the prior art, coating compositions for forming indium oxide layers were in general prepared from solutions comprising organic indium compounds; for example, the solution disclosed in U.S. Pat. No. 4,391,742 which comprises 100 parts of an indium compound and 5 to 20 parts of a stannic compound. The indium compound is an indium chelate obtained e.g. by reacting indium chloride dissolved in an inert solvent with methyl acetoacetonate and n-butyl alcohol, in the presence of triethylamine.

Therefore one of the objects of the present invention is the synthesis of indium alkoxides soluble in organic solvents, which can be used in coating compositions containing such solvents. It is also desired that said alkoxides be pure, in particular that they do not contain impurities susceptible to decrease the conductivity of the final oxide layers (for example Group IA metals). Moreover, said alkoxides should be obtained with a high yield for a low cost and to be easily isolated by simple methods, e.g. crystallisation. Said alkoxides which are inherently highly moisture sensitive, should also be stabilizable to facilitate their handling.

The preparation process according to the present invention allows to obtain indium alkoxides having all the above listed properties.

The synthesis according to the present invention consists in reacting a metal halide with an alcohol in basic medium, the said synthesis allowing the preparation of indium alkoxides with a wide range of alcohols and bases.

The preparation method consists in reacting in a one-step process an indium trihalide with a mixture comprising a $C_3$–$C_{20}$ alcohol and a strong base having a low nucleophilicity, in the presence of organic solvents, in anhydrous medium and under an inert gas.

In addition to the desired indium alkoxides, by-products due to the presence of the base are obtained. For example, if the halide is a chloride, the base forms with HCl evolved during the reaction a hydrochloride. The said hydrochloride can be separated from the alkoxide by known methods involving for example differences of solubility in organic solvents. However, in certain applications, such as coating to form indium oxide layers, the residual hydrochloride does not interfere since it is easily removed during the thermal treatments. The presence of the base also generates as by-product, an indium chloride/base complex, which is partly soluble in the reaction medium and difficult to remove. However its formation can be avoided, when desired, by selecting appropriate bases according to certain criteria explained below. It is important to note that for certain applications, when it is present in an amount less than 30%, it has no deleterious effects; for example, if conductive indium oxide films are to be formed, the said complex can act as a dopant.

In general, as indium halides, indium chloride or indium bromide are used.

Alcohols are selected so as to be soluble in the solvent used in the reaction, they must give alkoxides soluble in the coating solvents, and be able to react with the indium halide. Preferably, alcohols having a low molecular weight, soluble in common reaction solvents are used. However, alcohols such as methanol or ethanol are not appropriate since they give insoluble alkoxides. The alcohols according to the invention are $C_3$–$C_{20}$ alcohols, preferably saturated cyclic or aliphatic alcohols and most preferably cyclohexanol and primary alkanols.

For example, 2-propanol, 1-butanol, 2-butanol, 1-pentanol, cyclohexanol and 3-(trimethylsilyl)-1-propanol can be used, the preferred alcohols being 1-butanol, 1-pentanol, cyclohexanol, 3-(trimethylsilyl)-1-propanol.

According to the present invention, the bases must meet two requirements: they must be strong, i.e. have a pka higher than 10 and at the same time have a low nucleophilicity.

It is important to note that the nucleophilicity is a relative value which depends on the electrophile, the solvent and steric effects. An approximate ranking of nucleophilicity can be found in the literature, for example in J. March *Advanced Organic Chemistry*, 3rd Edition, John Wiley 1985, pp. 304–310.

With a base having a low nucleophilicity, the percentage of $InCl_3$/base complex is very low, or even nil with bases known as having a very low nucleophilicity, as 2,6-di-t-butylpyridine (DTBP), or 1,8-bis(dimethylamino)naphthalene (proton sponge). Conversely, the bases having a strong nucleophilicity such as ammonia, pyridine, imidazole, give percentages of complex close to 100%.

The bases both strong and having a low nucleophilicity can be selected e.g. among the bases cited in the *Fluka Chemika-Biochemika Catalog*, No 16 of 1988-1989 under the heading "Strong and Hindered Nitrogen Bases". Examples of said bases are trimethylamine; triethylamine; triisobutylamine; 1,1,3,3-tetramethylguanidine (TMG); 1,8-diazobicyclo[5.4.0]undec-7-ene (DBU); 1,5-diazabicyclo[4.3.0]non-5-ene (DBN); 2-tert-butylimino-2-diethylamino-1,3-dimethylperhydro-1,3,2-diazaphosphorine; 1,4-diazabicyclo[2.2.2]octane (Dabco); N,N-diisobutyl-2,4-dimethyl-3-pentylamine; N,N-diisopropyl-3-pentylamine; 3-dimethylamino-2,4-dimethylpentane; N-ethyldicyclohexylamine; N-ethyldiisopropylamine; 7-methyl-1,5,7-triazabicyclo-[4.4.0]dec-5-ene (MTBD); 1,2,2,6,6-pentamethylpiperidine; tributylamine and proton sponge already cited.

Reaction solvents are organic solvents compatible with the alcohol and the base selected. As solvent, the same alcohol as the alcohol forming the alkoxide can be used or any polar solvent having a polarity index $>3.5$, such as defined by L. Snyder in *J. Chromatography* 1978, 92, 223-224, having no OH group and forming no stable complex with indium chloride. Examples of solvents are chloroform, dimethylformamide, acetonitrile, tetrahydrofuran (THF), 1-butanol, dimethylformamide, pyridine, dimethylsulfoxide, acetonitrile, acetone, 1,4-dioxane, ethylacetate or mixtures thereof.

Preferred solvents are tetrahydrofuran, 1-butanol, dimethylformamide, acetonitrile or a mixture of THF/1-butanol.

It is to note that all the reactants should be strictly anhydrous.

Best results are obtained by adding indium chloride in organic solution to a base/alcohol mixture, which minimizes the complex formation. The reaction is carried out at temperatures between $-50°$ C. and $80°$ C., preferably about $0°$ C.

The following examples illustrate the invention.

EXAMPLE 1 Synthesis of Indium (III) 1-Tributoxide Using as Base Triethylamine Under argon, indium (III) chloride (35 mmol, 7.74 g) was dissolved in a mixture of hexane (50 ml) and 1-butanol (25 ml), dried azeotropically, and concentrated to a final volume of 50 ml. This solution was added dropwise to a solution of triethylamine (105 mmol, 10.62 g) in 1-butanol (25 ml) over 30 min at $0°$ C. Stirring was maintained for 30 min, after which time the supernatant solution containing the alkoxide and the $InCl_3$/base complex was removed from the precipitated salts by decantation. The salts were washed with 1-butanol (70 ml) to separate the solid hydrochloride from the solution, and the combined solutions evaporated under reduced pressure to leave the product as a viscous orange oil (9.5 g). NMR analysis of this product showed it to contain 90% indium (III) 1-butoxide and 10% indium chloride/triethylamine complex.

EXAMPLE 2 Synthesis of Indium (III) 1-Butoxide Using as Base Proton Sponge

Proton sponge (14.55 mmol, 3.12 g) and anhydrous 1-butanol (29.1 mmol, 2.16 g, 2.67 ml) were dissolved in anhydrous THF (20 ml). A solution of anhydrous indium (III) chloride (dried using molecular sieves) in anhydrous THF (9.7 mmol, 10 ml of 0.97 M solution) was added dropwise over 20 min at $0°$ C. Stirring was maintained for 18 h, whilst the temperature was allowed to rise to $22°$ C. At the end of this time, the solution was concentrated under reduced pressure and the resultant residue containing the alkoxide and proton sponge hydrochloride was washed with hexane ($2 \times 20$ ml), dissolved in anhydrous dichloromethane (20 ml), filtered to remove precipitated salts and evaporated under reduced pressure to leave the pure alkoxide/proton sponge hydrochloride mixture as a pale cream coloured powder, (6.31 g). This material was shown not to contain any indium chloride/base complex. 1H NMR analysis indicated that this corresponded to a yield of 62% of desired alkoxide.

EXAMPLE 3 Synthesis of Indium (III) 1-Butoxide From Indium Bromide

Indium (III) bromide (38.78 mmol, 13.75 g) was dissolved in a mixture of hexane (50 ml) and 1-butanol (50 ml), dried azeotropically, and concentrated to a final volume of 60 ml. This solution was added dropwise to a solution of triethylamine (116 mmol, 11.72 g) in 1-butanol (25 ml) over 30 min at $0°$ C. Stirring was maintained for 30 min, after which time the hydrobromide was washed with 1-butanol (50 ml). The solvents were removed under reduced pressure. The product was obtained as a viscous orange oil (12.3 g). NMR analysis of this product showed it to contain 89% indium (III) 1-butoxide and 11% indium bromide/triethylamine complex.

COMPARATIVE EXAMPLE 4

The example illustrates the effect of the alcohol nature on the alkoxide yield.

Under strictly identical reaction conditions (argon gas, solvent:THF, base:triethylamine) the following results were obtained

|     | Alcohol | Conversion to alkoxide % |
| --- | --- | --- |
| (1) | 2-propanol | 36 |
| (2) | 1-butanol | 92 |
| (3) | 2-butanol | 48 |
| (4) | 1-pentanol | 90 |
| (5) | cyclohexanol | 82 |
| (6) | 3-(trimethylsilyl)-1-propanol | 74 |

The example shows that the preferred alcohols according to the invention (2), (4), (5), (6) give better yields.

COMPARATIVE EXAMPLE 5

Similarly, indium (III)-cyclohexanoxides were obtained with various bases in similar conditions (argon gas, solvent:THF, alcohol:cyclohexanol), unless it is otherwise specified.

The following table reports the alkoxide conversion percentages with common bases, as determined 1H NMR.

|     | Bases | % alkoxide | % $InCl_3$/base complex |
| --- | --- | --- | --- |
| (1) | ammonia | 0 | 100 |
| (2) | pyridine | 0 | 100 |
| (3) | imidazole | 0 | 100 |
| (4) | TMG | 71 | 29 |

|      | Bases         | % alkoxide | % InCl₃/base complex |
|------|---------------|------------|----------------------|
| (5)  | DBU           | 71         | 29                   |
| (6)  | DBN           | 78         | 22                   |
| (7)  | trimethylamine| 75         | 25                   |
| (8)  | triethylamine | 82         | 18                   |
| (9)  | proton sponge*| 64         | 0                    |
| (10) | diethylamine**| 60         | 40                   |
| (11) | DTBP***       | 0          | 0                    |

*The theoretical quatity of hydrochloride was also obtained
** 1-butanol was used instead of cyclohexanol
***DTBP (2,6-di-t-butylpyridine) (pka 4.5 and having a low nucleophilicity). 1-butanol as used instead of cyclohexanol. No conversion was obtained.

It can be shown from the above results that only the bases according to the invention, (4), (5), (6), (7), (8), (9) provide indium alkoxides with high yields.

When it is desired to use said alkoxides for coating applications, e.g. to obtain indium oxide layers, the alkoxides can be stored before coating in alcohol under argon, e.g. if the alkoxide is indium (III) 1- butoxide in 1-butanol and stabilized with a small amount of acetic acid or acetylacetone.

We claim:

1. A process for the preparation of indium alkoxides soluble in organic solvents, wherein an indium halide is reacted in anhydrous medium and under inert gas in the presence of polar organic solvents with a mixture comprising a) a $C_3-C_{20}$ alcohol, b) a base selected among strong bases having a pka >10 and a low nucleophilicity.

2. A process according to claim 1, wherein said indium alkoxide is indium chloride or indium bromide.

3. A process according to claim 1, wherein said organic solvent is tetrahydrofuran, 1-butanol, dimethylformamide, acetonitrile, or a mixture of tetrahydrofuran and 1-butanol.

4. A process according to claim 1, wherein the alcohol is a $C_3-C_{20}$ saturated cyclic or aliphatic alcohol.

5. A process according to claim 4, wherein the $C_3-C_{20}$ saturated aliphatic alcohol is a primary alkanol.

6. A process according to claim 5, wherein said alcohol is 1-butanol, 1-pentanol, cyclohexanol or 3-(trimethylsilyl)-1-propanol.

7. A process according to claim 6, wherein said organic solvent is tetrahydrofuran, 1-butanol, dimethylformamide, acetonitrile, or a mixture of tetrahydrofuran and 1-butanol.

8. A process according to claim 1 carried out in one step.

9. A process according to claim 8, wherein said organic solvent is tetrahydrofuran, 1-butanol, dimethylformamide, acetonitrile, or a mixture of tetrahydrofuran and 1- butanol.

10. A process according to claim 9, wherein the alcohol is a $C_3-C_{20}$ saturated cyclic or aliphatic alcohol.

11. A process according to claim 10, wherein the $C_3-C_{20}$ saturated aliphatic alcohol is a primary alkanol.

12. A process according to claim 11, wherein said alcohol is 1-butanol, 1-pentanol, cyclohexanol or 3-(trimethylsilyl)-1-propanol.

13. A process according to claim 12, wherein said organic solvent is tetrahydrofuran, 1-butanol, dimethylformamide, acetonitrile, or a mixture of tetrahydrofuran and 1-butanol.

14. A process according to claim 8, wherein said indium alkoxide is indium chloride or indium bromide.

15. A process according to claim 1, wherein the alcohol is a $C_3-C_{20}$ saturated cyclic or aliphatic alcohol.

16. A process according to claim 15, wherein the $C_3-C_{20}$ saturated aliphatic alcohol is a primary alkanol.

17. A process according to claim 16, wherein said alcohol is 1-butanol, 1-pentanol, cyclohexanol or 3-(trimethylsilyl)-1- propanol.

18. A process according to claim 17, wherein said organic solvent is tetrahydrofuran, 1-butanol, dimethylformamide, acetonitrile, or a mixture of tetrahydrofuran and 1-butanol.

19. A process according to any of claims 1–18, wherein said base is trimethylamine, triethylamine, 1,1,3,3,-tetramethylguanidine (TMG), 1,8-diazabicyclo undec-7-ene (DBU), 1,5-diazobicyclo non-5-ene (DBN) or 1,8-bis(dimethylamino)naphthalene (proton sponge).

* * * * *